(12) United States Patent
Geiselhart

(10) Patent No.: US 8,133,224 B2
(45) Date of Patent: Mar. 13, 2012

(54) MEDICAL INSTRUMENT

(75) Inventor: Franz Geiselhart, Reutlingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 372 days.

(21) Appl. No.: 12/444,379

(22) PCT Filed: Sep. 26, 2007

(86) PCT No.: PCT/EP2007/008388

§ 371 (c)(1),
(2), (4) Date: Apr. 3, 2009

(87) PCT Pub. No.: WO2008/040485

PCT Pub. Date: Apr. 10, 2008

(65) Prior Publication Data

US 2009/0326531 A1    Dec. 31, 2009

(30) Foreign Application Priority Data

| Oct. 5, 2006 | (DE) | 10 2006 046 919 |
| Oct. 5, 2006 | (DE) | 10 2006 046 920 |
| Oct. 5, 2006 | (DE) | 10 2006 047 204 |
| Oct. 5, 2006 | (DE) | 10 2006 047 215 |
| Nov. 29, 2006 | (DE) | 10 2006 056 405 |
| Dec. 14, 2006 | (DE) | 10 2006 059 175 |

(51) Int. Cl.
*A61B 17/04* (2006.01)

(52) U.S. Cl. ............... 606/51; 606/207; 606/174

(58) Field of Classification Search ............ 606/42–52, 606/170, 174, 205–209
See application file for complete search history.

(56) References Cited

U.S. PATENT DOCUMENTS

| 5,431,674 A * | 7/1995 | Basile et al. ............ 606/170 |
| 6,775,575 B2 | 8/2004 | Bommannan et al. |
| 2002/0177849 A1 | 11/2002 | Schulze et al. |
| 2007/0293858 A1 | 12/2007 | Fischer |

FOREIGN PATENT DOCUMENTS

| DE | 44 21 822 | 10/1995 |
| DE | 44 44 166 | 6/1996 |
| DE | 44 44 166 A1 | 6/1996 |
| DE | 10 2004 026 179 | 12/2005 |
| EP | 0 717 960 | 6/1996 |
| EP | 717960 A2 * | 6/1996 |
| EP | 1 557 132 | 7/2005 |
| WO | WO 2005/072626 | 8/2005 |

OTHER PUBLICATIONS

English Translation of Written Opinion of the International Searching Authority.

* cited by examiner

*Primary Examiner* — Laura Bouchelle
(74) *Attorney, Agent, or Firm* — Dickstein Shapiro LLP

(57) ABSTRACT

A medical tubular shaft instrument for gripping and cutting tissue which provides a safe mode of operation. The instrument includes electrodes by which a mechanical contact between a blade and an associated cutting surface can be electrically determined. This determination allows the operating physician to be provided with sufficient information to determine whether the tissue that is to be severed has been successfully severed.

18 Claims, 9 Drawing Sheets

MEDICAL INSTRUMENT

FIELD OF THE INVENTION

The disclosed embodiments relate to a medical instrument, in particular a tubular shaft instrument, for cutting tissue.

BACKGROUND

In modern medicine, attempts are generally made to minimize damage to intact tissue. Thus, when circumstances permit, minimally invasive surgery is usually the preferred method of operative intervention used. Small incisions and minimal trauma to the tissue lead to less pain after the operation and to rapid recovery and mobilization of the patient. Laparoscopic surgery, during which complex operations are performed in the abdominal cavity, allows similar results.

Operations of this type, and the instruments required for them, present a particular challenge to the manufacturers of medical instruments since the majority of the operative steps are performed in very restricted spaces and without direct visual contact. Thus, the medical instruments used for these types of operations must not only be able to operate in the smallest spaces but must also function so reliably that visual monitoring is superfluous and unnecessary. The instruments are preferably constructed such that, even without visual contact, the operating surgeon always has feedback which enables him to draw conclusions about the progress of the operation.

This need applies to instruments that are suitable for the separation of tissue. Since scalpels having an open blade are, if anything, unsuitable for minimally invasive surgery (see, e.g., DE 44 44 166 A1), surgeons frequently resort to scissors-type or tong-type instruments having mouth parts. The mouth parts cover the blade during insertion of the instrument as well as hold the tissue to be cut. The blade is then displaced back and forth inside the mouth parts for cutting.

In the tong-like instruments, the blade or scalpel is usually covered completely by the associated mouth parts. It is, therefore, all the more difficult to draw conclusions as to whether the gripped tissue has already been completely separated with one or a plurality of cutting movements. This knowledge, however, is crucial for the positive progress of the operation.

On the other hand, excessively moving the blade when the tissue is already separated can quickly lead to wear on the instrument. It is necessary to check the instruments for their cutting ability and to replace worn blades. This form of maintenance is not only expensive but is also time-consuming. Often it is not possible to replace individual elements of the instruments, leading to the need to replace the entire instrument. Thus, excess wear should be avoided.

The object of the disclosed embodiments is to provide a medical instrument, which allows for reliable separation of tissue while providing long-lasting functionality.

SUMMARY

Disclosed embodiments include a medical instrument having a first and a second mouth part each with at least one clamping surface for fixing and/or positioning tissue in a fixing plane, a cutting device with a blade, which is disposed opposite one of the mouth parts for cutting tissue and is displaceable over a predetermined cutting path substantially parallel to the fixing plane, a first electrode and a second electrode, which are disposed on the cutting device and/or the clamping surface in such a manner that a mechanical contact between cutting and clamping surface is ascertainable by means of a processing unit connected to the electrodes.

The electrodes allow a mechanical contact between a blade and an associated clamping surface in a medical instrument for separating tissue to be ascertained. The mechanical contact may be ascertained electrically or by means of a switch. The processing unit receives the corresponding signals and evaluates them.

In a preferred embodiment, the blade may be the first electrode, the clamping surface may be the second electrode and the processing unit may be a device for determining an electrical resistance between the electrodes. The first electrode is thus formed by an electrically conductive blade or an electrically conductive section of the blade. The second electrode is the electrically conductive clamping surface or an electrically conductive section of the clamping surface. The processing unit measures the electrical resistance between the first and the second electrode. Preferably, the processing unit then ascertains that the tissue located immediately under the blade is separated when the resistance is lower that a preset threshold limit. This is necessary as the tissue to be cut has a certain electrical conductivity and consequently a high-ohm contact already exists between the first electrode and the second electrode when the tissue is unseparated. By specifying a threshold value, it is possible to differentiate the contact closure by way of the tissue to be cut from a direct contact closure between the two electrodes. This direct contact closure is an indicator for mechanical contact between blade and clamping surface.

The processing unit may be designed in such a manner that a curve of the resistance is ascertainable along the cutting path. The cutting path defines an observation interval for the processing unit and may, for example, include a back and forth movement of the blade between a distal and a proximal section of the mouth parts.

It is possible to detect the movement of the blade manually. Thus a mechanical limit stop during movement of the blade by means of an actuating device can provide information about the distance covered or about the cutting path covered. The processing unit includes a travel sensor and/or electric switch for detecting the displacement of the blade parallel to the clamping surface. The cutting device is designed such that it may be moved back and forth along a longitudinal axis of the medical instrument parallel to the clamping surface. The blade, therefore, should preferably separate the tissue not only at one point but over a cutting area along the previously described longitudinal displacement. To effectively determine whether the tissue is completely separated in this region, it is advantageous to record the blade's movement over an observation interval or an observation path and to determine whether there is a continuous mechanical contact between blade and clamping surface. The movement of the blade may be ascertained either directly by means of a travel sensor, or it may be ascertained indirectly by means of switches at the end of the cutting range whether the blade has been moved from a first switch to a second switch. Here too, the tissue is only deemed to have been completely separated when there is a mechanical or electrical, in particular a low-ohm, contact between blade and clamping surface within the entire interval or during the entire cutting path, that is to say from a movement of the blade from the first switch to the second switch.

The two mouth parts each may include a coagulation electrode for coagulation of the fixed tissue. Consequently, the tissue can be coagulated by means of a high-frequency current prior to mechanical separation by means of the blade. A safe closure of the vessels is ensured prior to mechanical separation. Furthermore, one of the two coagulation electrodes may be linked to the processing unit and thus be used to determine the mechanical contact. For formation of the coagulation electrodes, the mouth parts are either at least partially electrically conductive or they have an electrically conductive coating on the side facing towards the tissue.

The at least one mouth part may include a blade guide. The blade guide is used to stabilize the blade during the cutting movement. Furthermore, the blade guide may have the previously described switches or travel sensors in order to determine the blade's movements.

The medical instrument has means for emitting a signal, which is emitted when the resistance drops below a predetermined minimum value over the entire cutting path. This form of display may thus be used not only to determine the resistance and hence the progress at a point or at a position of the blade when separating tissue, but also to determine a complete separation of the tissue over the entire cutting path.

BRIEF DESCRIPTION OF THE DRAWINGS

The disclosed embodiments will be described in more detail with reference to exemplary embodiments, which will be explained in greater detail with reference to the enclosed drawings.

DETAILED DESCRIPTION

Figure 1:
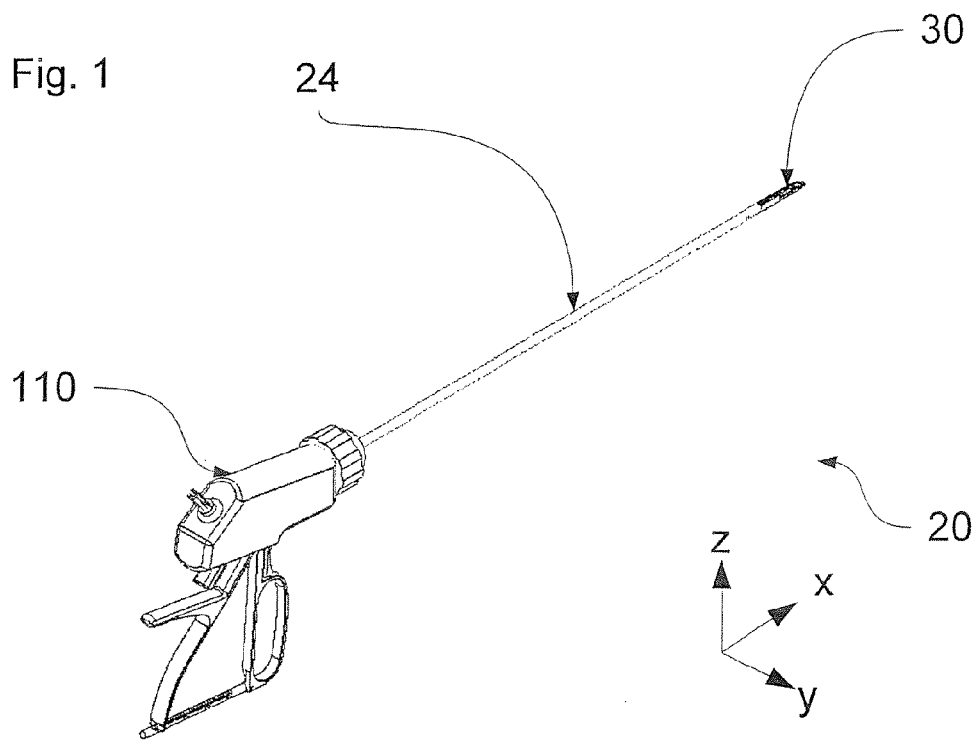
FIG. 1 illustrates a tubular shaft instrument for separating tissue.

The same reference numerals are used in the following description for identical parts and parts acting in an identical manner.

FIG. 1 provides a rough overview of a disclosed embodiment of a tubular shaft instrument 20. It shows three functional components of the tubular shaft instrument 20—a handle 110, a longish tubular shaft 24 and a tool head 30 disposed on the distal end of tube shaft 24. Tool head 30 provides the tubular shaft instrument's actual functionality. It is used for cutting and/or coagulating tissue. Handle 110 controls the movement of tool head 30. In particular, for fixing, coagulating and cutting tissue mouth parts 10, 10' (see, e.g., FIG. 2) may be opened and closed by handle 110.

Figure 2:
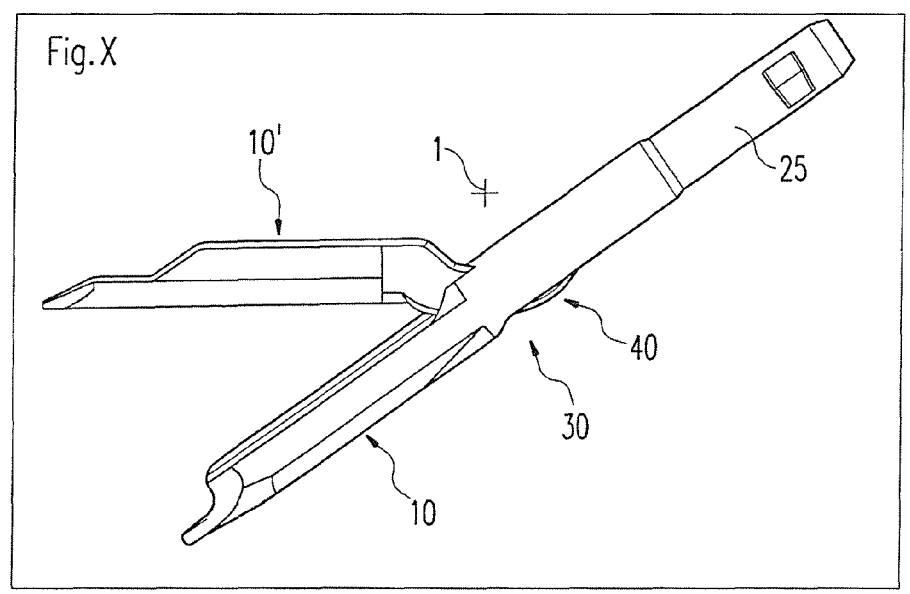
FIG. 2 illustrates the tool head of the tubular shaft instrument from FIG. 1, including a first and a second mouth part.

FIG. 2 shows one disclosed embodiment of a tool head 30 that includes a first mouth part 10 and a second mouth part 10'. First mouth part 10 is an oblong body having on its side facing tubular shaft 24 an adapter 25, which is rigidly joined to the previously described tubular shaft 24. Second mouth part 10' is attached to first mouth part 10 by way of an articulation 40 and may be brought from an open position for seizing the tissue into a closed position for fixing the tissue. Articulation 40 is designed such that a virtual fulcrum 1 or pivot is located outside first and second mouth parts 10, 10'. Unlike conventional articulations 40 for such instruments, fulcrum 1 is not, therefore, located in the region where mouth parts 10, 10' engage each other or in the tubular shaft 24 close to the longitudinal axis of tube shaft 24. The illustrated mechanism of articulation 40 acts such that a virtual fulcrum 1 is created above the side of the tubular shaft instrument which faces second mouth part 10'.

Figure 9:
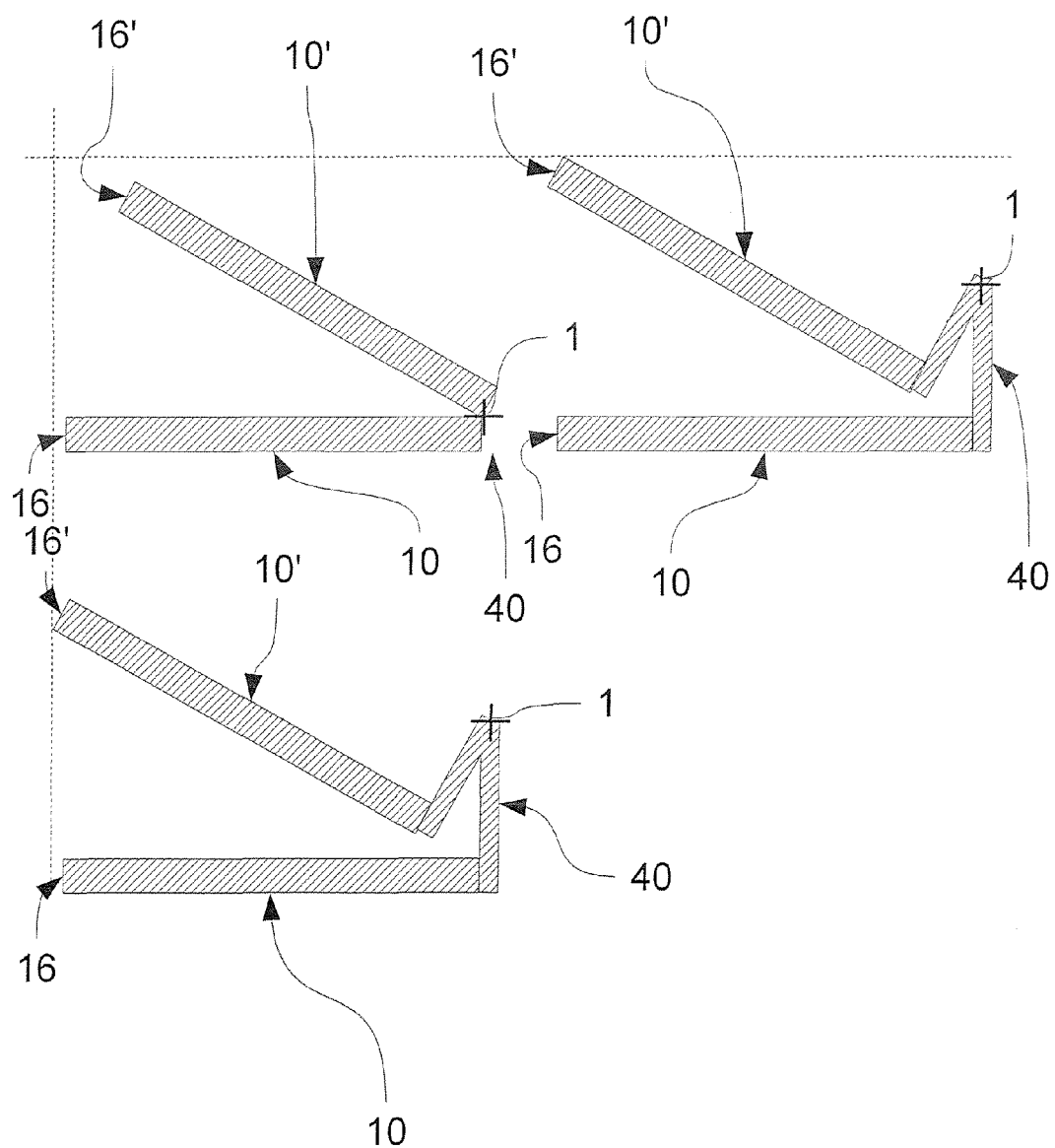
FIG. 9 is a schematic diagram of two different articulations.

One advantage of such a relocated fulcrum 1 is now described with respect to the schematic diagrams of FIG. 9. Illustrated in the top left-hand corner of FIG. 9 is a conventional articulation 40, the fulcrum 1 of which is located substantially on the longitudinal axes of mouth parts 10 and 10'. In the open position, tip 16' of second mouth part 10' is offset backwards relative to tip 16 of first mouth part 10. However, as can be seen in the other two diagrams of FIG. 9 (which illustrate a disclosed embodiment) this is not the case. Instead, in disclosed embodiments, fulcrum 1 is located noticeably above the longitudinal axes of both oblong mouth parts 10, 10'. With the same opening in respect of the angle formed by first mouth part 10 relative to second mouth part 10', tip 16' of second mouth part 10' is located substantially on or in front of a perpendicular straight line through tip 16 of first mouth part 10, even in the open state. If second mouth part 10' is opened relative to first mouth part 10, there is not only a rotary displacement during which the relative alignment of second mouth part 10' changes relative to first mouth part 10 but there is also a longitudinal displacement of second mouth part 10' which is oriented distally, that is to say parallel to the longitudinal axis of first mouth part 10 in the direction of its tip 16. Conversely, during a closing movement of mouth parts 10, 10', there is a longitudinal displacement of second mouth part 10' in the proximal direction. As a result of this, tissue which is located between both mouth parts 10, 10', is ultimately drawn into tool head 30. Furthermore, according to the disclosed embodiments, the lift of second tip 16, that is to say the distance between first and second tip 16, 16', is considerably greater with the same opening angle (see, e.g., FIG. 9, right-hand side as compared to left-hand side). In one disclosed embodiment, the length of mouth parts 10, 10' relative to the distance of the longitudinal axis of first mouth part 10 to the fulcrum is in the ratio of approximately 10:1.

Figure 3:
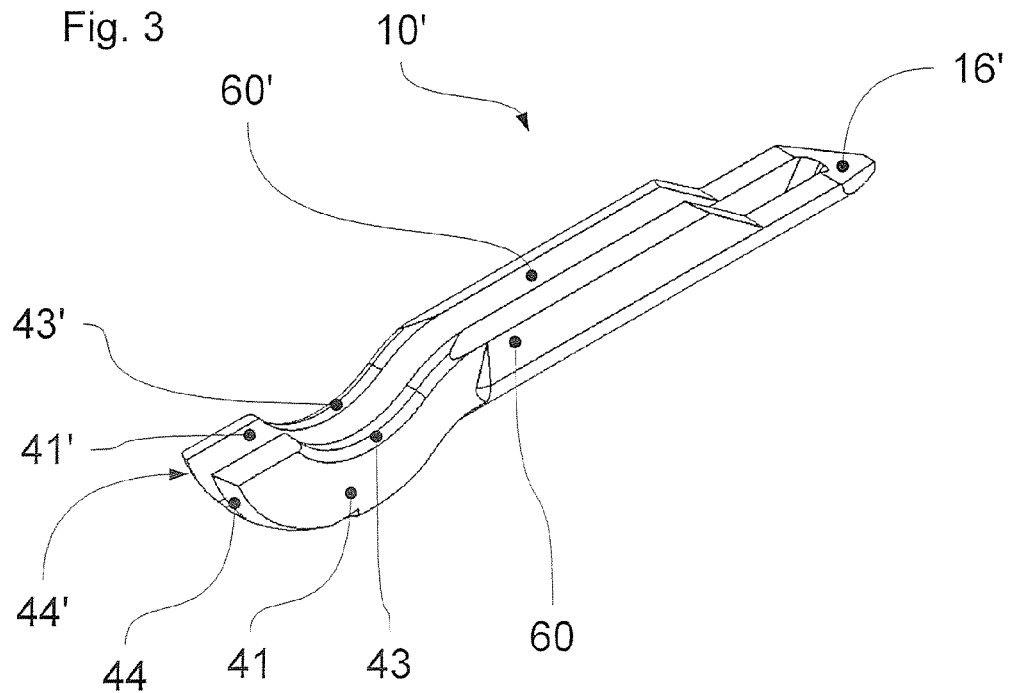
FIG. 3 illustrates the second mouth part of FIG. 2 in a perspective lateral view.
Figure 4:
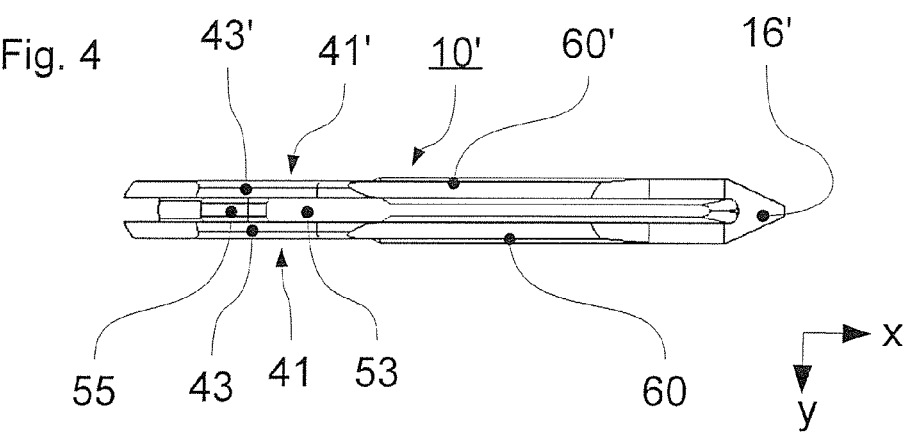
FIG. 4 illustrates the second mouth part of FIG. 2 in a view from above.

While in FIG. 9 relocated fulcrum 1 is achieved, for the sake of illustration, by way of extensions attached vertically on the proximal ends of mouth parts 10, 10', in a preferred embodiment, the formation of fulcrum 1 is purely virtual. This virtual design is achieved by a slotted guide system as is explained below on the basis of FIGS. 3-8. Thus, as shown in FIG. 3, second mouth part 10' has two curved articulation guide rails 41, 41' on its proximal end opposing tip 16'. Seen from above (FIG. 4), these articulation guide rails 41, 41' run substantially parallel along the longitudinal axis of second mouth part 10' and are spaced apart to form a channel.

Figure 5:
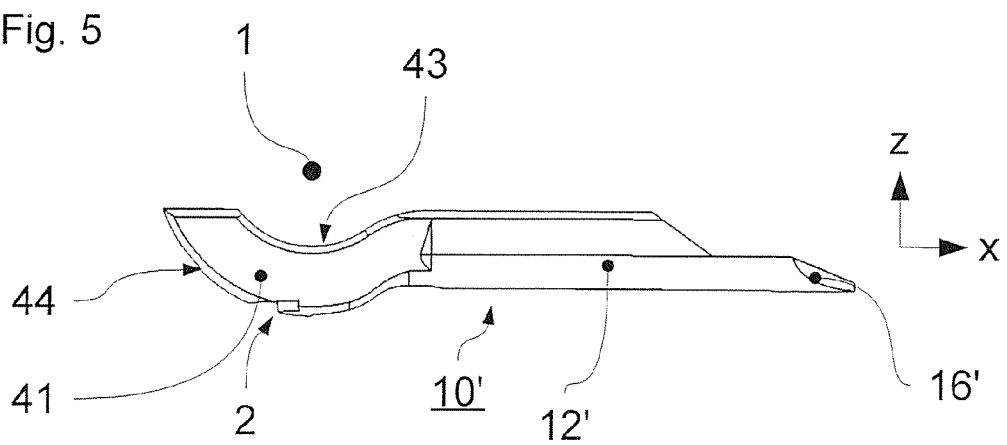
FIG. 5 illustrates the second mouth part of FIG. 2 in a lateral view.
Figure 6:
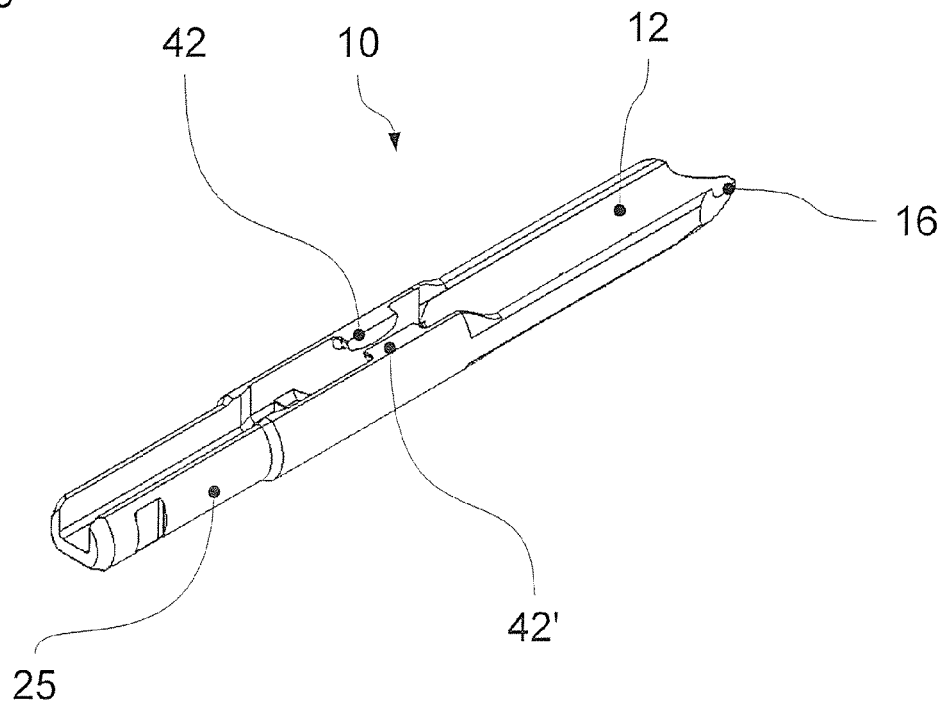
FIG. 6 illustrates the first mouth part of FIG. 2 in a perspective lateral view.
Figure 7:
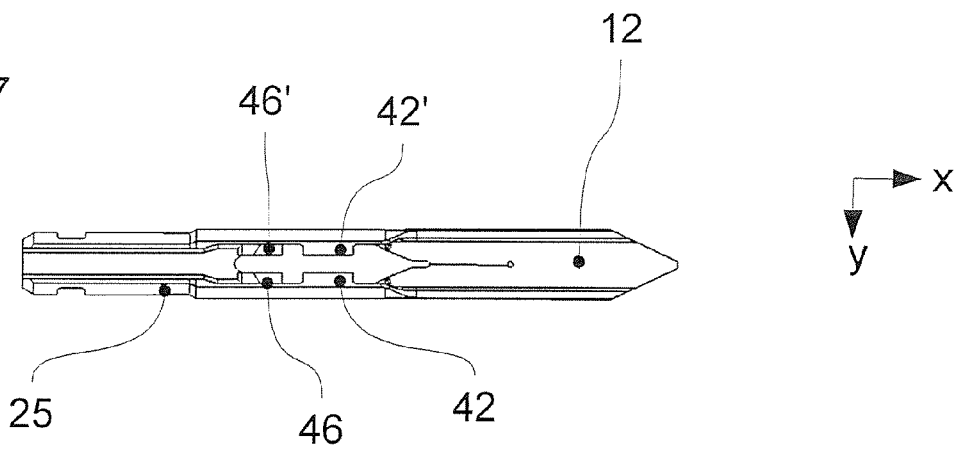
FIG. 7 illustrates the first mouth part of FIG. 2 in a view from above.
Figure 8:
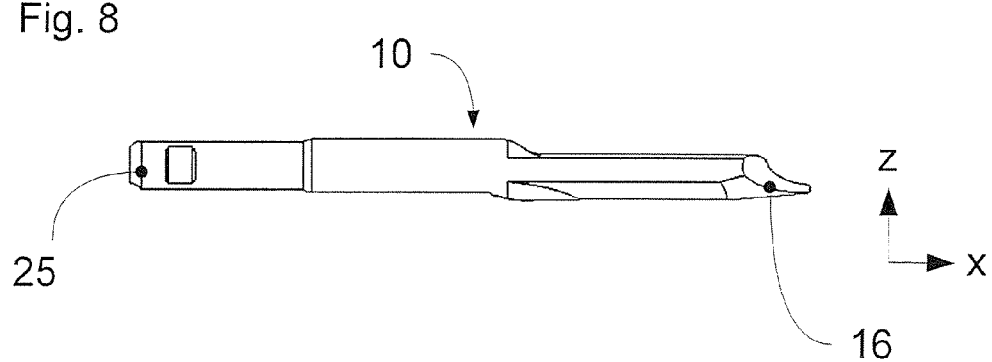
FIG. 8 illustrates the first mouth part of FIG. 2 in a lateral view.

Seen from the side (see, e.g., FIG. 5), second mouth part 10' has a spoon-shaped profile. The proximal end of second mouth part 10', in particular articulation guide rails 41, 41', thus each have on their upper side a concave section 43, 43', which engages with first mouth part 10. As can be seen in FIG. 6, mouth part 10 has two articulation guide pins 42, 42', each of which has a convex structural section. During the opening and closing movement of mouth parts 10, 10', concave section 43 of first articulation guide rail 41 slides over the adjacent, convex section of first articulation guide pin 42 and concave section 43' of second articulation guide rail 41' slides over the adjacent, convex section of second articulation guide pin 42'. The curvature of concave sections 43, 43' of both articulation guide rails 41, 41' and the corresponding sections of articulation guide pins 42, 42' determine the position of virtual fulcrum 1. With a more pronounced curvature, fulcrum 1 lies closer to tool head 30 than it does with a less pronounced curvature. The effects described with respect of FIG. 9 thus occur correspondingly more or less pronounced than as described with respect to FIG. 9.

Compared to articulations that only have a single-point connection, the guide mechanisms or articulation 40 additionally have the advantage of high stability. Due to the convex and concave sections which engage with each other, a large-area contact region is formed and articulation 40 can absorb significantly more force than an articulation having a single-point connection. To further stabilize articulation 40, first mouth part 10 includes a first articulation guide bearing 46 and a second articulation guide bearing 46'. Like articulation guide pins 42, 42', articulation guide bearings 46, 46' are attached alternately on the inside of the sidewalls of first mouth part 10.

First articulation guide bearing 46 and first guide pin 42 are spaced apart such that they accommodate first articulation guide rail 41 in the space between them. First articulation guide bearing 46 has a concave cross-section, which engages with convex section 44 of first articulation guide rail 41. On opening and closing the tool head 30, first articulation guide rail 41, guided by first guide pin 42 and first articulation guide bearing 46, rotates about fulcrum 1.

Likewise, second articulation guide rail 41', guided by second guide pin 42' and articulation guide bearing 46', rotates about fulcrum 1. Second articulation guide rail 41', second articulation guide pin 42', a convex section 44' of second articulation guide rail 41' and second articulation guide bearing 46' are designed for rotation and are disposed symmetrically to first articulation guide rail 41, first articulation guide pin 42, convex section 44 of first articulation guide rail 41 and first articulation guide bearing 46.

Figure 10:
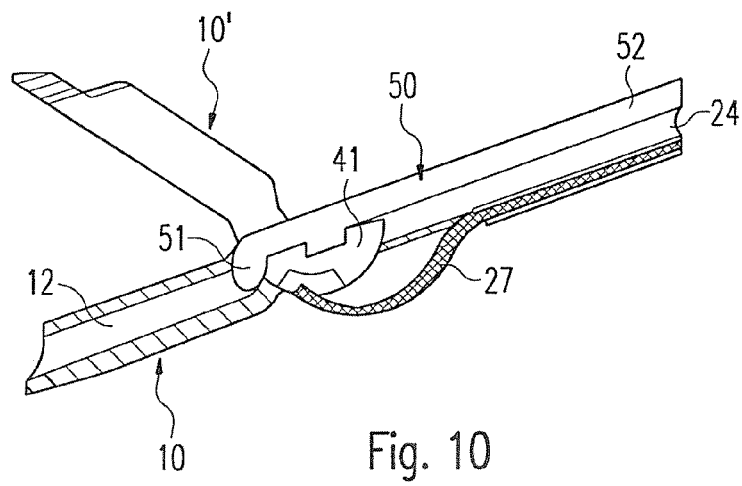
FIG. 10 illustrates a cross-section through the tool head of FIG. 2 with a cutting device.
Figure 19:
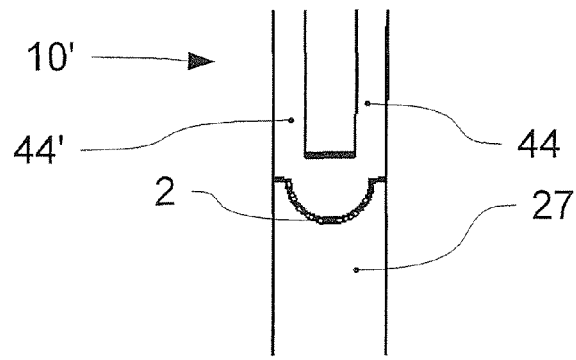
FIG. 19 illustrates the second mouth part of FIG. 2 with a tension strip.

As shown in FIG. 10, a tension strip 27 is attached on the proximal end of second mouth part 10'. More precisely, it is attached approximately centrally on convex sections 44, 44' of articulation guide rails 41, 41'. To achieve this, articulation guide rails 41, 41' have a profile for forming an abutting edge 2 (FIG. 5). Preferably, this abutting edge 2 does not run in a straight line parallel to fulcrum 1, but is instead designed in a semi-circular shape (see, e.g., FIG. 19). Due to this elongated abutting edge 2, along which second mouth part 10' and tension strip 27 are welded, the transmission of force into tension strip 27 is homogenized and the tensile and flexural loading capacity of the weld is significantly increased. In alternative embodiments, acute-angled welds or welds with multiple serrations, which provide a comparable result, are conceivable. Tension strip 27 is substantially wider than it is thick parallel to fulcrum 1. This ensures resilience and bendability of tension strip 27 upon rotation of the second mouth part 10'. In the longitudinal direction of the tubular shaft instrument, however, tension strip 27 is relatively stiff such that shear forces may also be generated.

By attaching a first end of tension strip 27 to convex sections 44, 44' of articulation guide rails 41, 41', it is ensured that the tensile force exerted by means of tension strip 27 always acts substantially tangentially to the circular motion of curved articulation guide rails 41, 41' about fulcrum 1. Thus, a uniform transmission of force independent of the opening angle is assured. A second end of tension strip 27 is operatively connected to handle 110 and may be displaced by means of a control device provided thereon. Due to virtual fulcrum 1, which, as already explained, is located outside and above mouth parts 10, 10', the distance between fulcrum 1 and the first end of tension strip 27 is significantly greater than the distance achieved with normal articulations. Thus, the embodiment of the described tubular shaft instrument has a significantly higher leverage by means of which second mouth part 10' may be moved over tension strip 27.

Each of mouth parts 10, 10' has a clamping surface 12, 12' for fixing the tissue. First mouth part 10 thus has, on a distal section, a first clamping surface 12 which faces upwards. First clamping surface 12 is formed to be substantially concave transverse to the longitudinal axis of first mouth part 10. In the closed state of tool head 30, convex second clamping surface 12' of second mouth part 10' lies substantially parallel to this first clamping surface 12.

In one disclosed embodiment, these clamping surfaces 12, 12' are not only suitable for securely fixing the tissue to be cut later, they also form the electrodes for a coagulation process. To achieve this, sections of clamping surfaces 12, 12' are electrically conductive and connected via printed conductors to a high-frequency current source, which is also controllable by way of handle 110. Thus the gripped tissue may be cauterized to such an extent prior to the cutting procedure that separation is possible without bleeding. Preferably, sections at least of mouth parts 10, 10' are manufactured from ceramic material by injection molding. Thus the guide elements, in particular articulation guide rails 41, 41' and articulation guide pins 42, 42' of articulation 40, are easy to form. Forming articulation 40 of ceramic material creates an electrical insulation between mouth parts 10, 10', in particular between their electrodes for coagulation.

Figure 11:
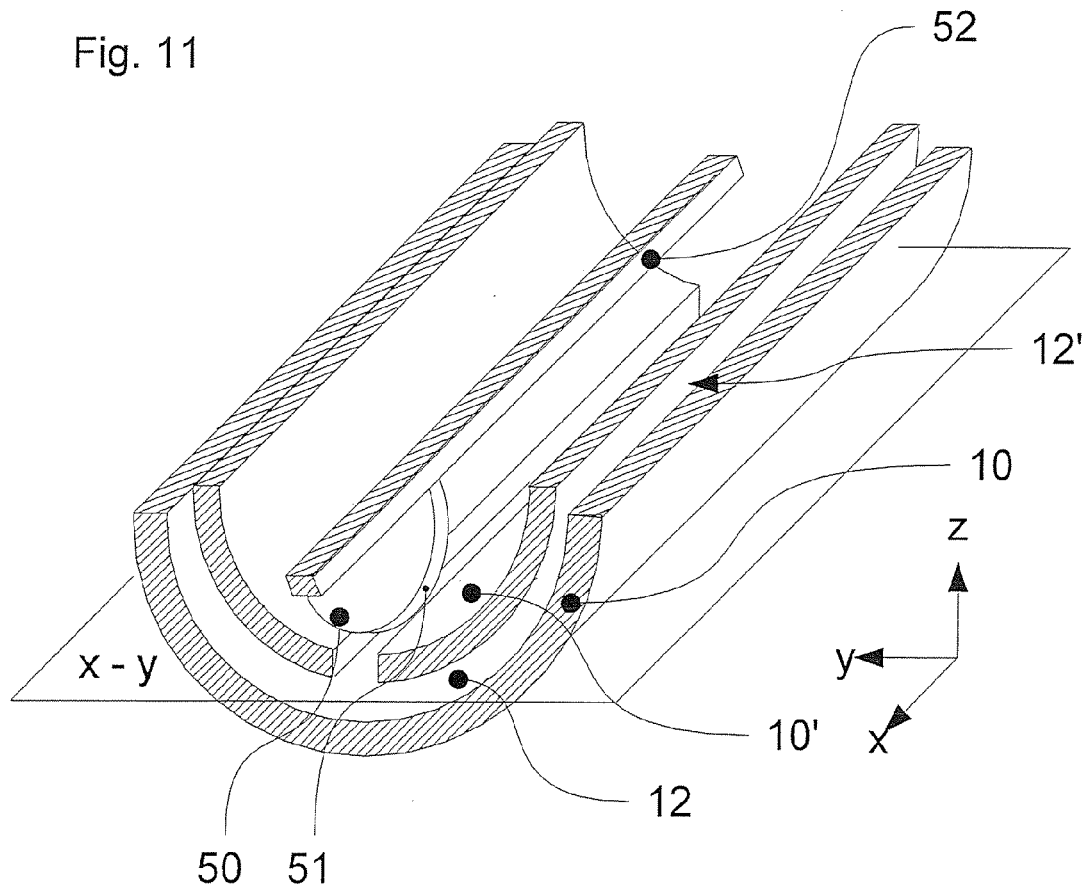
FIG. 11 is a schematic diagram of the cutting device.

In one disclosed embodiment, the actual mechanical cutting process takes place after coagulation. To achieve this, a cutting device 50 is moved parallel to a fixing plane x-y (see, e.g., FIG. 11), which is defined by clamping surfaces 12, 12'. This cutting device 50 includes a blade 51 for separating the tissue in addition to a guide wire 52 by means of which a displacement of blade 51 in the longitudinal direction of the tubular shaft instrument (x-axis) is possible.

Prior to the cutting process, blade 51 is drawn back towards tubular shaft 24 far enough that premature injury of the tissue is not possible. Preferably, the blade in first mouth part 10 is at the level of articulation guide pins 42, 42'. From this starting position, blade 51 is brought onto fixing plane x-y by way of a ramp 55 integrated in second mouth part 10' (see, e.g., FIG. 4). This ramp 55 is located between the two articulation guide rails 41, 41'. Second mouth part 10' provides a blade guide 53 for the displacement of blade 51 or the cutting device 50. This blade guide 53 is an oblong opening extending along the longitudinal axis of second mouth part 10'. In order to hold blade 51 perpendicular to fixing plane x-y, second mouth part 10' has side parts 60, 60' in a central region. The side parts 60, 60' are disposed parallel to each other such that they form a channel extending lengthways. Blade 51 or the cutter is guided in this channel.

Figure 12:
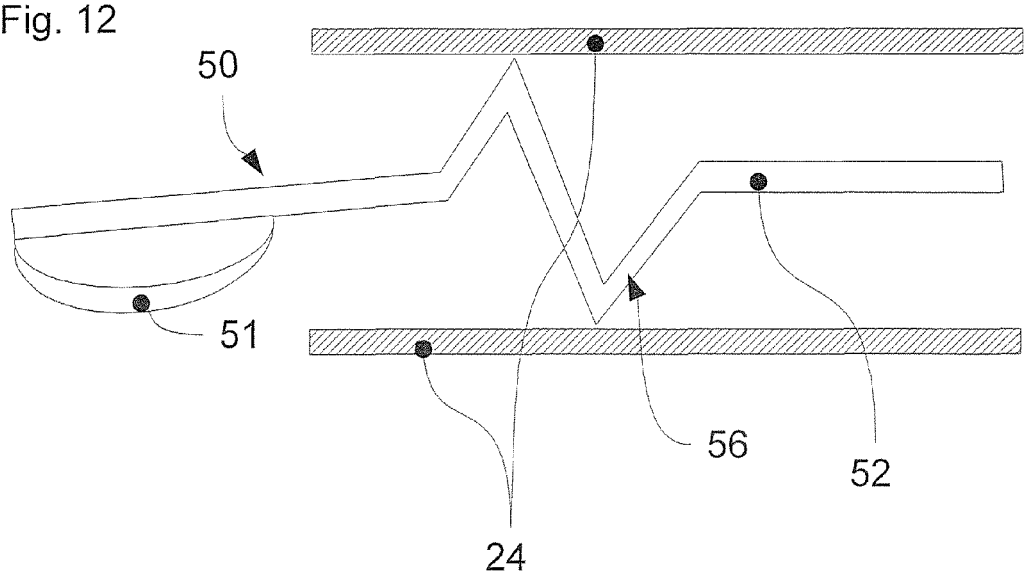
FIG. 12 is a schematic view of the cutting device in a tubular shaft of a tubular shaft instrument.

After closing mouth parts 10, 10', blade 51 thus glides out of its starting position over ramp 55 into the previously described channel and may there be pulled or pushed distally and proximally over the tissue. Blade 51 is preloaded relative to fixing plane x-y in order to ensure that this displacement separates the tissue step-by-step. A preloading device exerts a force perpendicular to fixing plane x-y, which presses blade 51 against the plane. This force is built up via the resilience of guide wire 52 and its curvature. As can be seen from FIG. 12, guide wire 52 is curved perpendicular to fixing plane x-y in the plane preloaded by blade 51. A crimp 56 is located in a front section of guide wire 52. Crimp 56 is integrated in guide wire 52 in such a manner that in the fully extended state of cutting device 50, that is to say when blade 51 is at the distal end of mouth parts 10, 10', the crimp in tubular shaft 24 is likewise at the distal end of the shaft. Crimp 56 is used to transfer at least part of the force exerted by the curvature of guide wire 52 perpendicular to fixing plane x-y to tubular shaft 24 and has corresponding contact points. The curvature of guide wire 52 is provided such that if the proximal end of the guide wire runs parallel to tubular shaft 24, the distal end of unattached guide wire 52 is curved downwards and blade 51 lies at least partially below fixing level x-y. Guide wire 52 is operatively connected to handle 110 in such a manner that blade 51 can be moved back and forth in tool head 30 by means thereof.

Various other embodiments are conceivable with respect to the design of blade 51. These will be described in the following on the basis of FIGS. 13, 14 and 15. One idea of the disclosed embodiment is that blade 51 has at least one section which runs substantially parallel to fixing plane x-y and thus parallel to the fixed tissue. Consequently, during the cutting procedure, blade 51 glides over the tissue until it is completely separated. Unlike in conventional cutting procedures, it can thus be ensured that even when blade 51 is blunt the tissue will be separated and will not be crushed due to the mechanical pressure. The section of the cutting blade formed parallel to fixing plane x-y likewise has the advantage that blade 51 rests on the tissue not only at a single point but usually over a longer region. Therefore, the wearing of blade 51 at only certain points is prevented.

Figure 13:
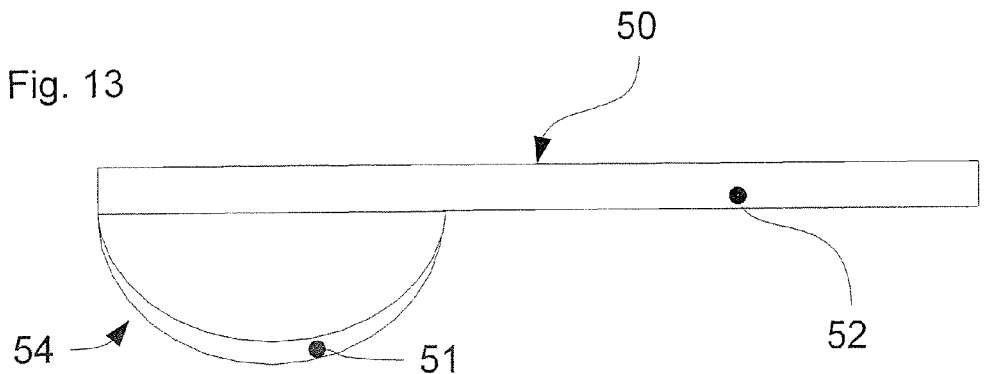
FIG. 13 illustrates an embodiment of a cutting blade.

FIG. 13 shows a semicircular blade 51, having a convex curvature. Blade 51 is disposed on the underside of guide wire 52. It has a blade curvature 54 distally and proximally to the tubular shaft instrument.

Figure 14:
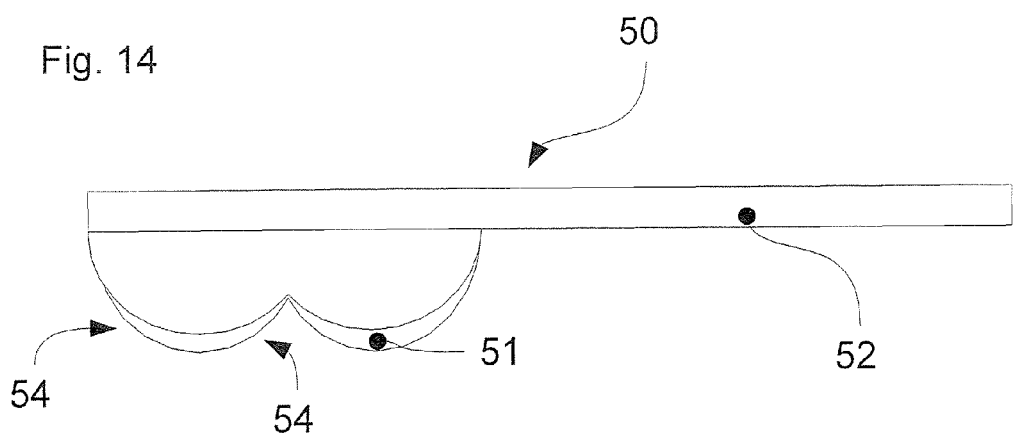
FIG. 14 illustrates another embodiment of a cutting blade.

FIG. 14 shows a blade 51, comprising two semicircles each disposed one behind the other.

Figure 15:
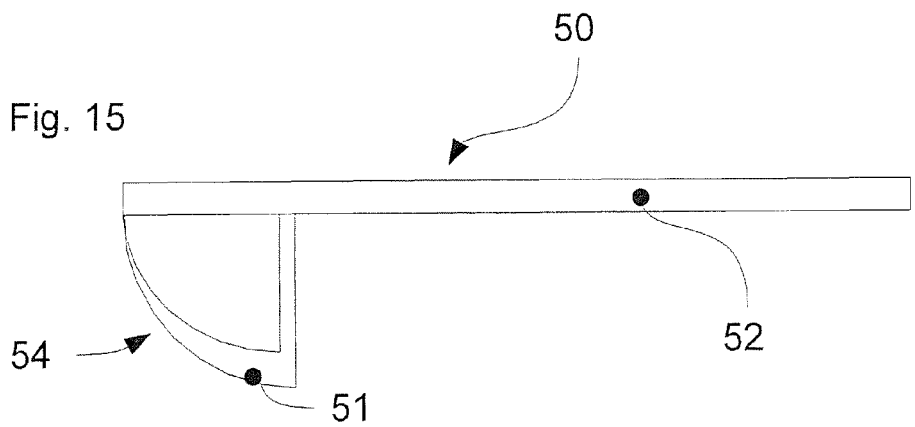
FIG. 15 illustrates another embodiment of a cutting blade.

FIG. 15 shows a blade 51, having a blade curvature 54 distally, and a section perpendicular to guide wire 52 proximally.

Preferably, blade 51 includes microteeth.

In another disclosed embodiment (see, e.g., FIG. 10), guide wire 52 is a rail. The rail may be designed in such a manner that is has the same functionality as guide wire 52. Preloading relative to fixing plane x-y may be achieved by means of the rail's intrinsic resilience or by means of a separate device (e.g., a spring).

The cutting device 50 of the disclosed embodiments has been described so far as being used in conjunction with the advantageous articulation shape. Both disclosed embodiments, however, may also be executed separately from one another.

Figure 17:
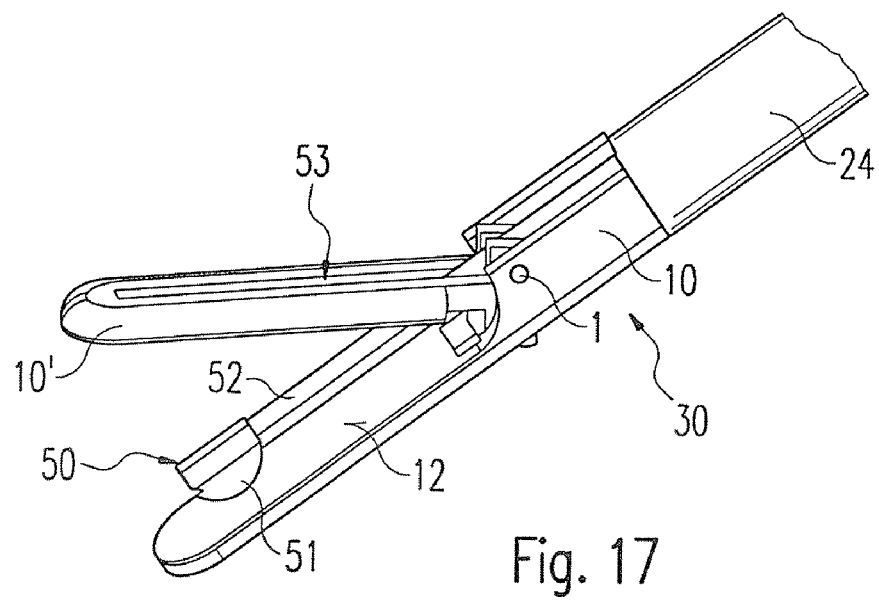
FIG. 17 illustrates a perspective view of a tool head in an open position.
Figure 18:
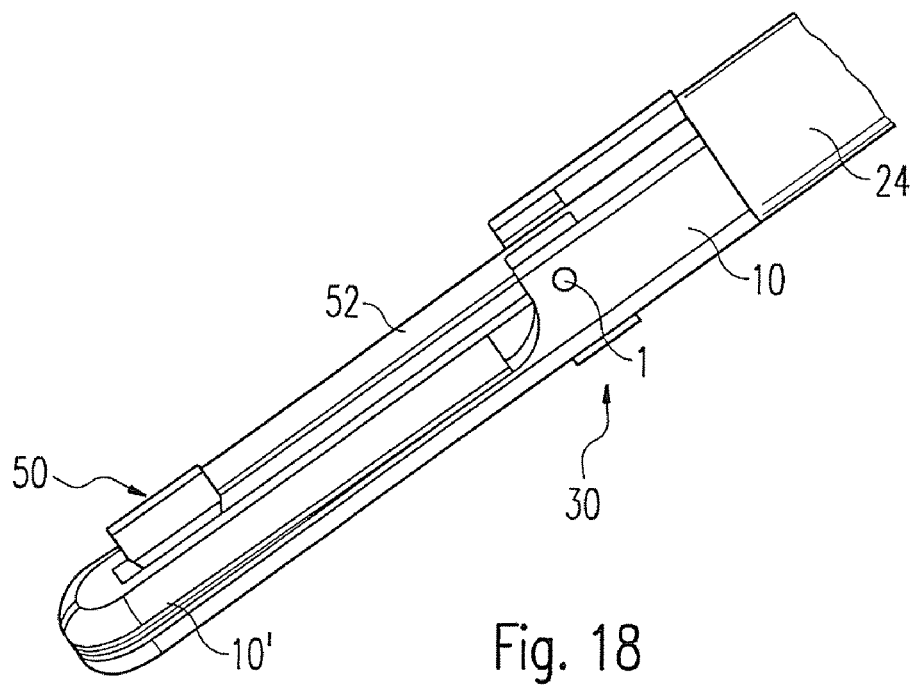
FIG. 18 illustrates the tool head of FIG. 17 in a closed position.

Thus, FIGS. 17 and 18, for example, show cutting device 50 in a tool head 30, whereby second mouth part 10' is not in operative connection with first mouth part 10 by way of a slotted guide system. Here fulcrum 1 lies substantially on the longitudinal axis of mouth parts 10, 10'

Figure 16:
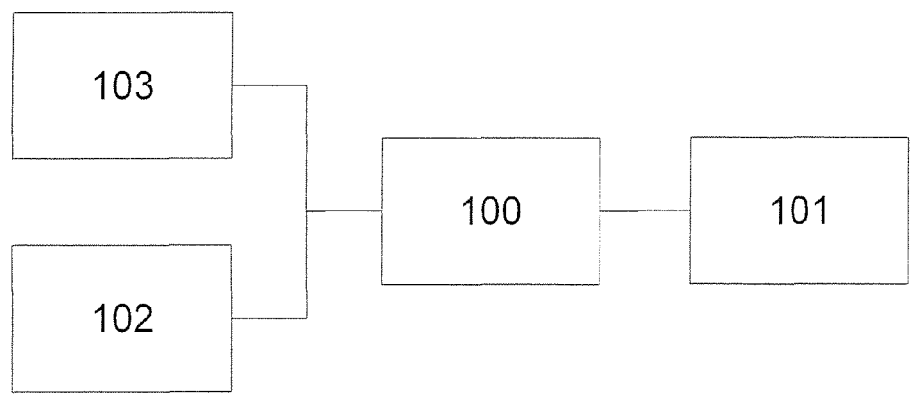
FIG. 16 illustrates a block diagram of an incision monitoring device.

In another disclosed embodiment, the tubular shaft instrument includes a cut monitoring device. This device determines when the tissue between the two clamping surfaces 12, 12' is completely separated. In a disclosed embodiment, when the tissue is completely separated blade 51 rests on first clamping surface 12. Since clamping surface 12 includes an electrode for coagulation, at least a portion of the clamping surface 12 is electrically conductive. According to a disclosed embodiment, at least one section of blade 51, which mechanically contacts separating surface 12 when the tissue is separated, is likewise formed of an electrically conductive material. The electrical contact between blade 51 and clamping surface 12 is determined by a cut monitoring device. The gripped tissue is deemed to be completely separated when a continuous electrical contact exists between blade 51 and clamping surface 12 during a complete cutting movement by tip 16' of second mouth part 10' up to ramp 55. As can be seen from FIG. 16, the cut monitoring device includes a processing unit 100, a display device 101, a switch 103 and a travel sensor 102 for determining and displaying the progress of the cutting procedure. Travel sensor 102 determines the position or displacement of blade 51 and consequently helps to define an observation period that preferably covers a complete blade movement. Switch 103 is formed, in the simplest case, by electrically conductive blade 51 and first clamping surface 12. Since the tissue to be cut has a certain electrical conductivity, electric switch 103 is only deemed to be closed when a low-ohm connection exists between clamping surface 12 and blade 51. A corresponding device is connected upstream of processing unit 100. If processing unit 100 ascertains that there is a continuous low-ohm contact between blade 51 and clamping surface 12 during a complete observation period, it indicates to the user (by means of display device 101) that the gripped tissue has been completely separated. Since the displacement of blade 51 over clamping surface 12 without tissue sandwiched between damages the device, the indication of complete separation allows the cutting to stop, thus protecting cutting device 50.

Alternatively, it may also be constantly indicated to the user whether there is a direct mechanical contact between blade 51 and clamping surface 12. As the user performs the movement of blade 51 manually, he can draw conclusions independently as to whether the tissue is adequately separated.

In another disclosed embodiment, travel sensor 102 includes two electrical contact regions on the distal and proximal ends of blade guide 53, which are designed in such a manner that it is possible to determine contact between blade 51 and the distal contact region as well as between blade 51 and the proximal contact region. Processing unit 100 can thus determine the start and end of the observation interval.

Figure 20:
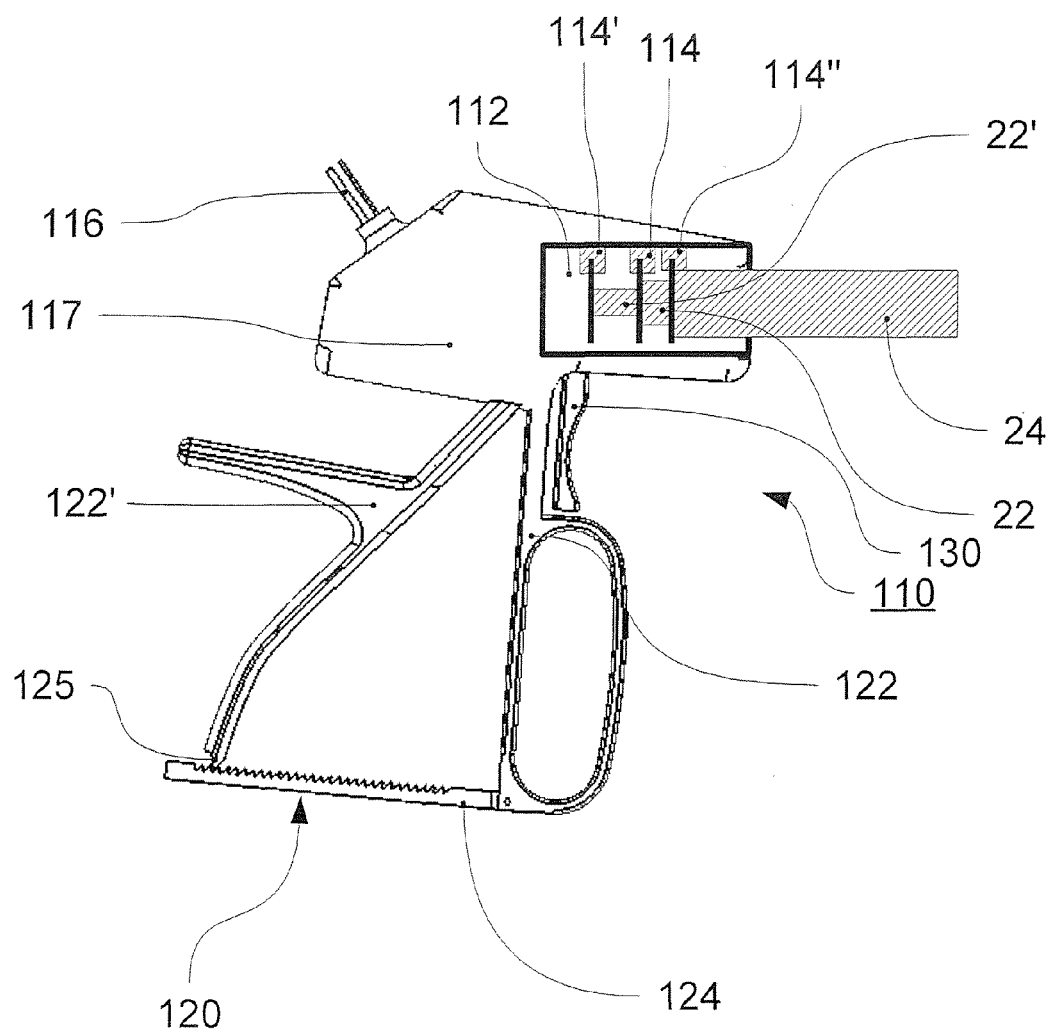
FIG. 20 is a schematic lateral view of the tubular shaft instrument of FIG. 1.

FIG. 20 shows a schematic detail view of handle 110 of FIG. 1. Handle 110 includes a handle body 117 having a first handle lever 122 integrally formed on the underside thereof. Handle lever 122 has an opening for receiving a plurality of fingers, preferably the middle, ring and little finger. A second handle lever 122' is rotatably joined to handle body 117 close to first handle lever 122. Mouth parts 10, 10' of tool head 30 may be opened and closed by means of a proximal and distal displacement of second handle lever 122' relative to first handle lever 122. Handle levers 122, 122' form a hand trigger 120 and can thus be grasped in the user's hand such that the entire tubular shaft instrument can be guided with one hand. To achieve this, the hand encloses sections of handle lever 122, 122'. An extension 125 (which engages in a toothed rack 124) is located on the end of second handle lever 122' facing away from handle body 117. This toothed rack 124 is attached at a right angle to the longitudinal axis of first handle lever 122 on its end facing away from handle body 117. The teeth of toothed rack 124 are designed in such a manner that second handle lever 122' can be moved step by step towards handle lever 122 and the correspondingly set position remains without a continued exertion of a force. In order to release this fastening of handle levers 122, 122' to each other, toothed rack 124 is pressed away from extension 125 such that they are no longer engaged.

Handle 110 has a finger trigger 130, which is likewise rotatably attached to handle body 117. Cutting device 50, in particular blade 51, may be displaced distally by operating finger trigger 130. A spring element (not illustrated) inside handle body 117 returns finger trigger 130 to its starting position after operation, as a result of which cutting device 50 is displaced proximally. Finger trigger 130 is disposed distally in front of first handle lever 122 in such a manner that finger trigger 130 can be operated with the first finger on grasping handle levers 122, 122'.

Handle 110 has a momentary contact switch 116 on the proximal side of handle body 117, which controls the coagulation current. In an alternative embodiment, it is possible to provide a control device having a plurality of actuating elements by means of which a plurality of coagulation modes may be selected and performed, instead of momentary contact switch 116. It is likewise conceivable to provide display device 101 on handle body 117.

In one disclosed embodiment, tubular shaft 24 and handle 110 are designed in such a manner that tubular shaft 24 may be detachably inserted into handle 110. To achieve this, a receiving opening 112, which can be closed by means of a cover, is located on the side of handle 110.

Thus, prior to the operation, a sterile disposable tubular shaft 24 having appropriate tool head 30 and cutting device 50 is inserted into reusable handle 110 and locked therein. Reuse of tubular shaft 24 and the associated devices is not envisaged. Handle body 117 has a first coupling element 114, a second coupling element 114' and a third coupling element 114" for mechanical connection of tool head 30, cutting device 51 and tubular shaft 24. A ring provided on the proximal end of tubular shaft 24 engages with third coupling element 114" in such a manner that the tubular shaft is rigidly connected to handle body 117. A first inner tube adapter 22 engages, by means of a ring likewise disposed on the proximal end, with first coupling element 114, which is in operative connection with second handle lever 122'. The displacement of second handle lever 122' is transferred to first coupling element 114 by means of a mechanism disposed inside handle body 117 and transfers this displacement in turn to first inner tube adapter 22. This is directly or indirectly joined mechanically to second mouth part 10' by way of tension strip 27. A longitudinal displacement of first inner tube adapter 22 relative to tubular shaft 24 thus brings about opening and closing of mouth parts 10, 10'.

A second inner tube adapter 22' is disposed movably relative to first inner tube adapter 22 inside the first inner tube. This inner tube adapter 22' is operatively connected to guide wire 52 and displaces blade 51. Inserting tubular shaft 24 into handle body 117 engages a proximal ring on the end of second inner tube adapter 22' with second coupling element 114' and transfers the displacement or the force exerted by means of finger trigger 130 to cutting device 50.

In order to make it easier to insert disposable tubular shaft 24, a removable fastening is provided thereon, which holds inner tube adapter 22, 22' in a predetermined position relative to tubular shaft 24. The tubular shaft 24 is designed in such a manner that the rings are easily insertable into coupling elements 114, 114', 114"

Coupling elements 114, 114', 114" are designed such that tubular shaft 24 may be rotated relative to handle 110. Thus the alignment of tool head 30 can be adjusted freely relative to handle 110. During rotation, the rings of inner tube adapters 22, 22' and of tubular shaft 24 rotate in coupling elements 114, 114', 114" and thus form an articulation.

It should be pointed out here that all the above described parts and in particular the details illustrated in the drawings are essential for the disclosed embodiments alone and in combination. Adaptations thereof are the common practice of persons skilled in the art.

The invention claimed is:

1. A medical instrument comprising:
   a first mouth part and a second mouth part, each mouth part having at least one clamping surface for fixing and/or positioning tissue in a fixing plane;
   a cutting device having a blade, which is disposed opposite one of the mouth parts for cutting tissue and is displaceable along a predetermined cutting path that is substantially parallel to the fixing plane;
   a first electrode and a second electrode, disposed on the cutting device and/or the clamping surface, such that a mechanical contact between blade and clamping surface may be ascertained by a processing unit connected to the electrodes;
   a tubular shaft joined to the first and second mouth parts;
   an actuating device whereby the blade is displaceably guided substantially parallel to the fixing plane; and
   a preloading device whereby the blade is preloaded by a flexible element against a fixing plane during cutting.

2. The medical instrument according to claim 1, wherein the blade comprises the first electrode, the clamping surface comprises the second electrode and the processing unit comprises a device for determining an electrical resistance between the first and second electrodes.

3. The medical instrument according to claim 2, wherein the processing unit allows a curve of the resistance to be ascertainable along the cutting path.

4. The medical instrument according to claim 2, further comprising a means for emitting a signal when the resistance over the entire cutting path falls below a predetermined minimum value.

5. The medical instrument according to claim 1, wherein the processing unit comprises a travel sensor for detecting the displacement of the blade parallel to the clamping surface.

6. The medical instrument according to claim 1, wherein each of the first and second mouth parts comprises a coagulation electrode for coagulating the fixed tissue.

7. The medical instrument according to claim 1, wherein at least one of the first and second mouth parts comprises a blade guide.

8. The medical instrument according to claim 1, wherein the preloading device comprises a resilient guide wire—having a curvature, and wherein the guide wire is substantially rigidly joined to the blade and is guided in the tubular shaft such that the blade is preloaded in relation to the tubular shaft in the direction of the fixing plane.

9. The medical instrument according to claim 1, wherein the preloading device includes a crimped section, which is disposed in the guide wire such that it is close to the distal end of the tubular shaft when the blade is pushed forward.

10. The medical instrument according to claim 1, further comprising a ramp-shaped blade guide, wherein the blade guide is configured such that, by moving in the direction of cutting the blade is brought out of a starting position at a distance from the fixing plane onto the fixing plane.

11. The medical instrument according to claim 1, wherein the first and second mouth parts are disposed rotatably to one another and the blade guide is configured such that the blade may be brought into a starting position close to a fulcrum of the first and second mouth parts.

12. A medical instrument according to claim 1,
wherein the tubular shaft accommodates the first and second mouth parts, and further comprising
at least one articulation for rotatably supporting the first and second mouth parts such that the first and second mouth parts may be brought from an open position into a closed position in order to fix the tissue using the clamping surfaces,
wherein the articulation is configured such that a fulcrum of the articulation is located outside the first and second mouth parts and the distal end of at least one of the first and second mouth parts is displaceable away from the distal end of the tubular shaft when the first and second mouth parts are brought into the open position.

13. The medical instrument according to claim 12, wherein the articulation comprises a slotted guide system.

14. The medical instrument according to claim 12, wherein the articulation comprises an articulation guide on one of the first and second mouth parts and at least one rail or groove on the other of the two mouth parts.

15. The medical instrument according to claim 12, wherein at least two partial articulations are provided, which are spaced apart from one another to form a passage disposed centrally between said partial articulations.

16. The medical instrument according to claim 12, further comprising a strip that can be displaced substantially linearly for opening and closing of a mouth part to be displaced, said strip being attached by a resilient end section on the mouth part to be displaced.

17. The medical instrument according to claim 1, wherein the medical instrument is an electrosurgical tubular shaft instrument.

18. The medical instrument according to claim 1, wherein the processing unit comprises an electric switch for detecting the displacement of the blade parallel to the clamping surface.

* * * * *